(12) United States Patent
Pacifico et al.

(10) Patent No.: US 10,751,036 B1
(45) Date of Patent: Aug. 25, 2020

(54) DEVICE FOR THE APPLICATION OF SURGICAL MATERIALS TO TISSUE

(71) Applicant: Abyrx, Inc., Irvington, NY (US)

(72) Inventors: John Pacifico, Irvington, NY (US);
Frank Do, Irvington, NY (US);
Richard L. Kronenthal, Irvington, NY (US); Aniq Darr, Irvington, NY (US)

(73) Assignee: Abyrx, Inc., Irvington, NY (US)

( * ) Notice: Subject to any disclaimer, the term of this patent is extended or adjusted under 35 U.S.C. 154(b) by 162 days.

(21) Appl. No.: 16/165,339

(22) Filed: Oct. 19, 2018

Related U.S. Application Data

(63) Continuation of application No. 14/850,025, filed on Sep. 10, 2015, now Pat. No. 10,201,338.

(60) Provisional application No. 62/049,835, filed on Sep. 12, 2014, provisional application No. 62/048,597, filed on Sep. 10, 2014.

(51) Int. Cl.
| | |
|---|---|
| *A61B 17/00* | (2006.01) |
| *A61B 17/88* | (2006.01) |
| *A61L 24/04* | (2006.01) |
| *A61L 24/06* | (2006.01) |
| *A61B 17/11* | (2006.01) |

(52) U.S. Cl.
CPC .... *A61B 17/0057* (2013.01); *A61B 17/00491* (2013.01); *A61B 17/11* (2013.01); *A61B 17/8805* (2013.01); *A61L 24/04* (2013.01); *A61L 24/046* (2013.01); *A61L 24/06* (2013.01); *A61B 2017/00884* (2013.01); *A61B 2017/00893* (2013.01); *A61B 2017/00933* (2013.01); *A61B 2017/00946* (2013.01); *A61L 2300/80* (2013.01)

(58) Field of Classification Search
CPC .......... A61B 17/00491; A61B 17/0057; A61B 17/11
See application file for complete search history.

(56) References Cited

U.S. PATENT DOCUMENTS

| | | | |
|---|---|---|---|
| 5,356,629 A | 10/1994 | Sander et al. | |
| 7,074,425 B2 | 7/2006 | Constantine et al. | |
| 7,270,813 B2 | 9/2007 | Shimp et al. | |
| 7,553,913 B2 | 6/2009 | Wellisz et al. | |
| 7,829,616 B2 | 11/2010 | Wellisz et al. | |
| 7,914,819 B1 | 3/2011 | Wen et al. | |
| 7,955,616 B2 | 6/2011 | Kronenthal | |
| 7,989,000 B2 | 8/2011 | Kronenthal | |
| 8,022,178 B2 | 9/2011 | Horii et al. | |
| 8,182,527 B2 * | 5/2012 | Llanos | A61L 31/16 623/1.46 |
| 8,299,032 B2 | 10/2012 | Yokoi et al. | |
| 8,974,503 B2 * | 3/2015 | Brunner | A61B 17/80 606/281 |
| 9,827,349 B1 | 11/2017 | Pacifico et al. | |
| 10,201,338 B1 | 2/2019 | Pacifico et al. | |
| 2009/0082540 A1 | 3/2009 | Bezwada | |

(Continued)

FOREIGN PATENT DOCUMENTS

| | | |
|---|---|---|
| WO | WO-201303652 A1 | 1/2013 |
| WO | WO-2013067154 A1 | 5/2013 |

*Primary Examiner* — Christian A Sevilla
(74) *Attorney, Agent, or Firm* — Cooley LLP; Ivor R. Elrifi; Matthew Pavao

(57) ABSTRACT

The invention relates to a device comprising a surgical material and a support material and related methods for the application of the surgical material to a wound or surgical site using the device.

18 Claims, 2 Drawing Sheets

(56) References Cited

U.S. PATENT DOCUMENTS

2010/0137902 A1\* 6/2010 Lee ................. C09J 171/02
606/213

\* cited by examiner

DEVICE FOR THE APPLICATION OF SURGICAL MATERIALS TO TISSUE

RELATED APPLICATIONS

This application is a continuation of U.S. application Ser. No. 14/850,025, filed Sep. 10, 2015, which claims priority to U.S. Application No. 62/049,835, filed Sep. 12, 2014 and to U.S. Application No. 62/048,597, filed Sep. 10, 2014, each of which is incorporated by reference herein in its entirety.

FIELD OF THE INVENTION

The present invention relates to surgical devices and related methods for tissue repair.

BACKGROUND OF THE INVENTION

Bone hemostatic materials are either wax-like, putty-like, or paste-like in consistency. Waxlike materials such as bone wax and Ostene™ must be warmed and kneaded to soften them into a putty-like consistency for application to bleeding bone. Other commercially available putty-like hemostatic materials such as Hemasorb™, Hemasorb Plus™, and Absorbable Hemostatic Bone Putty (AHBP™) do not require warming or kneading prior to application to bone.

When the bleeding bone surface is elongated and narrow such as the medially-divided sternum, application of hemostatic materials using conventional surgical manipulation is more difficult. The present invention addresses the need to provide a more effective means for applying hemostatic and other, e.g., antimicrobial, putty-like materials to the surface of bleeding bone during a surgical procedure.

A new construct concept has been developed to provide a more surgically convenient method for applying hemostatic and drug-containing materials to bleeding surfaces. This concept can be applied to surfaces of any anatomical dimension. Another advantage of this construct is that it may offer protection from damage to surgical gloves by sharp bone surfaces.

SUMMARY OF THE INVENTION

The invention relates to a device comprising a surgical material and a support material and related methods for the application of the surgical material to a wound or surgical site using the device. In one aspect, the device comprises the surgical material in the form of a ribbon or sheet contained between two layers of the support material (e.g., a top layer and a bottom layer). In one aspect, the two layers of the support material are not in contact with each other. The device may be of any suitable length to width ratio and is adapted to be cut using common surgical instruments into an appropriate sized segment or shape for application to a wound surface or surgical site. The size of the appropriate sized segment or shape will depend upon the geometry of the wound or surgical site. The device is flexible and can be folded. The support material is non-adhesive to surgical gloves so that the device can be manipulated with gloved hands without adhering to the gloves. Thus, alternatively, or in addition to cutting, the device maybe folded into an appropriate sized segment or shape for application to a wound surface or surgical site.

The support material may be constructed from body-absorbable or non-absorbable components, or it may comprise a mixture of body-absorbable and non-absorbable components. Each layer of the support material may be made of the same or different material. The support material maybe dyed or pigmented, or it may be uncolored. The support material may be in the form of a mesh. The mesh may be a microporous mesh, having pore sizes of less than 10 microns; or the mesh may be a macroporous mesh, having pore sizes of greater than 75 microns. Preferably, for hard tissue applications, the support material is body-absorbable.

In one aspect, the support material is constructed from a synthetic or natural absorbable polymer, e.g., polyglycolic acid, polylactic acid, copolymers of lactic and glycolic acids, collagen, cross-linked alginic acid, etc.

In one embodiment, the support material is a fabric material comprising body-absorbable and non-absorbable components. In one embodiment, the body-absorbable component of the fabric material comprises or consists of fibers of polyglycolic acid or polydioxanone, or a mixture of the two. In one embodiment, the non-absorbable component of the fabric material comprises or consists of fibers of, for example, polypropylene, polyethylene terephthalate or nylon, or a mixture of the latter two. The fabric material can be prepared from monofilament or multifilament fibers in varying fiber densities and may be flat-bed or circularly knitted or woven or non-woven in construction. Knitted fabrics are preferred to woven because they are less prone to fraying, if cut.

In one embodiment, the fabric material is knitted or woven from monofilament or multifilament fiber. The physical characteristics of the fabric are controlled primarily by the denier, tenacity and modulus of the fiber and the density and geometry of the knit or weave constructions. The fiber may be absorbable, e.g., polyglycolic acid multifilament or polydioxanone monofilament, or it may be non-absorbable, e.g., polyethylene terephthalate multifilament or nylon or polypropylene monofilament.

In one embodiment, the fabric material consists of a non-woven polymer fabric. In one aspect, the non-woven polymer fabric comprises or consists of a non-absorbable polymer such as Tyvek™ (DuPont) which is spun-bonded high density polyethylene. In another aspect, the non-woven polymer fabric is body-absorbable.

In another embodiment, the support material is a film. The film may be continuous or appropriately fenestrated. Film thickness maybe determined by the modulus of the polymer employed, i.e., the higher the modulus, the thinner the film can be made. Further, to prevent the surgical material from sticking to the film, the film can be prepared from a polymer or a polymer mixture having a low surface energy, e.g., poly(propylene), poly(tetrafluoroethylene) or a silicone polymer (a polyalkylsiloxane).

In one embodiment, the surgical material is in the form of a putty having a viscosity of from of from 250,000-100,000,000 (cP at 20 C) and may be, for example, a hemostatic material, a bone void filler, a bone graft extender, a bone cement, or an antimicrobial, analgesic, antineoplastic, anti-inflammatory, radiopaque, osteoconductive and/or osteoinductive material. In one embodiment, the surgical material is a putty or paste, for example as represented by the tradenames Hemasorb™, Hemasorb Plus™, and Absorbable Hemostatic Bone Putty (AHBP™).

In one aspect, the surgical material is a putty that acts as a mechanical hemostat when applied to the bleeding surface of hard or soft tissue. The term mechanical hemostat is meant to convey a material that is effective to stop bleeding without the use of chemical agents, e.g., pro-coagulants. Mechanical hemostasis or tamponade refers to mechanically blocking the bleeding pores or canals of the cut or damaged bone to arrest hemorrhage. This is distinguished from chemical hemostasis which utilizes chemical means to promote the clotting of blood.

In one embodiment, the device is particularly adapted for application of surgical pastes and putties to hard tissues, such as cut bone or cartilage. In one aspect of the methods described herein, the device is used to apply the surgical material to at least one surface of a wound, or to a surgical site. In one aspect, the method is a method for hemostasis of actively bleeding hard tissue, such as bone, the method comprising removing one layer of a support material to expose one surface of a hemostatic surgical material, applying the exposed surface of the hemostatic material to at least one surface of the bleeding bone by pressing the exposed surface of the surgical material onto the surface of the hard tissue until it adheres to the bone tissue, and then removing the second layer of support material from the surgical material.

In another aspect, the device is used in a method for removing unwanted surgical material from a wound or surgical site. This is accomplished by removing the support material and, with it, the adhering, unwanted surgical material to be discarded.

In one aspect, the device is used in a method for providing mechanical hemostasis to a wound or surgical site by applying the hemostatic material to at least one surface of the wound, or to the surgical site, which maybe actively bleeding. In some surgical procedures, the device maybe used to apply the hemostatic material to at least two surfaces of the wound, such as two surfaces of a cut bone, thereby providing mechanical hemostasis at one or more bleeding surfaces of the wound or at the surgical site.

In one embodiment, the device is in the form of an elongated ribbon suitable for use on sternum edges, skull flap edges, and at the site of reapproximated tissues.

In another embodiment, the device is in the form of sheet in the shape of a square or rectangle. In this form, the device can be cut into any desired shape and size and wrapped around tissues or blood vessels or be placed on or between tissue surfaces.

The surgical advantages of the present device relate to its ability to be cut and/or folded into a preferred shape that adheres to itself and, wrapped in one or more layers on or around a bleeding surface, adheres to either or both the wound surface and/or itself (similar to the geometry of a sphygmomanometer cuff) to provide various thicknesses and shapes to accommodate different anatomical surfaces and degrees of bleeding severity.

The device maybe manufactured, for example, by producing a putty-like ribbon of the hemostatic material, optionally by extrusion through a die, and placing the hemostatic material between two layers of the support material.

DETAILED DESCRIPTION OF THE INVENTION

Figure 1:
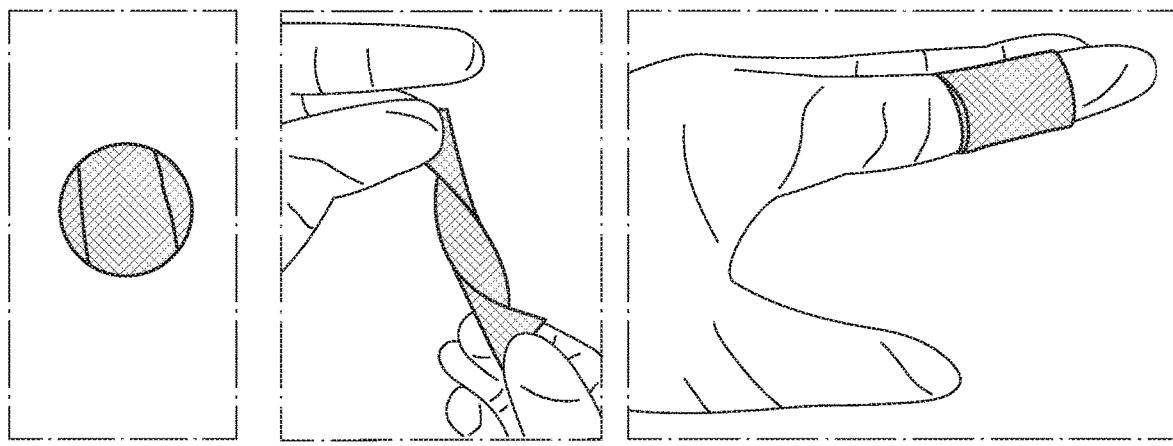
FIG. 1: a ball prepared from a strip of fabric-putty laminate, 2 shows a twisted ribbon of fabric-putty laminate and 3 shows several layers of a fabric-putty laminate strip wrapped around a gloved finger.
Figure 2:
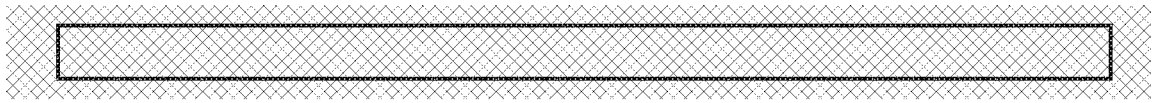
FIG. 2: an extruded strip of surgical material (e.g., hemostatic putty) sandwiched between two layers of knitted, pigmented polypropylene fabric.

The invention relates to a device that provides mechanical assistance for the application of surgical materials to a wound or surgical site. The device comprises a surgical material and one or two layers of a support material. The surgical material is typically in the form of a layer of putty or paste and the support material is typically in the form of a mesh or film layer. A layer of surgical material is typically in the range of 0.1 to 5 cm thick, preferably about 0.1 to 0.5 cm thick, and the mesh or film layer may be in the range of about 0.1 to 0.6 mm thick, preferably about 0.3 mm, 0.4 mm, or 0.5 mm thick. The mesh may be a microporous mesh, having pore sizes of less than 10 microns; or the mesh may be a macroporous mesh, having pore sizes of greater than 75 microns. The support material may be body-absorbable or non-absorbable. The surgical material may also be body-absorbable or non-absorbable. The device can be cut into any desired shape or size, for example to wrap it around blood vessels or cut tissue. In one embodiment, the device is in the form of an elongated ribbon suitable for use on sternum edges, skull flap edges, and at the site of reapproximated tissues. In another embodiment, the device is in the form of sheet in the shape of a square or rectangle.

In one embodiment the surgical material is a high viscosity material, e.g., a material having a viscosity in the range of 250,000-100,000,000 (cP at 20 C). Surgical materials in this range of viscosity are suitable for hard tissue (e.g., bone, cartilage) applications. In a particular embodiment, the surgical material is in the form of a putty having a viscosity of from of from 250,000-100,000,000 (cP at 20 C). The term "putty" refers to a composition that is soft, moldable, preferably non-elastic, and cohesive. In one aspect, the surgical material is in the form of a putty that is moldable by hand at room temperature. Suitable surgical putties are described, for example, in WO 201303652 and U.S. Ser. No. 14/553,847, each of which is incorporated herein by reference in its entirety.

In another embodiment, the surgical material has a viscosity in the range of 1000-250,000 (cP at 20 C). Surgical materials in this range of viscosity are suitable for soft tissue applications. Thus, for soft tissue applications the surgical material is generally of a lower viscosity and may be in the form of a soft putty, gel or paste. Typically for soft tissue applications the support material is the form of a non-body absorbable mesh or film.

The device is typically manufactured as a ribbon or sheet of at least one layer of a support material and at least one layer of a surgical material. But the device may be cut or manipulated into different shapes. In one embodiment, the device is in the form of a ribbon or sheet. In another embodiment, the device is in the form of a square, rectangle, circle, or cylinder.

In one embodiment, a single layer of surgical material is contained between two layers of a support material. In one embodiment, the device contains only one layer of support material and one layer of surgical material in contact with one surface of the support material. In another embodiment, a single layer of support material is between two layers of the surgical material.

In one embodiment, the surgical material forms a continuous surface in contact with a surface of at least one layer of support material. In another embodiment, the surgical material is in the form of droplets spaced at a controlled or variable distance from each other on a surface of at least one layer of support material. In one embodiment, the droplets are spaced at a distance of from about ⅛ inch to 3 inches apart. In one embodiment, the support material of the device is impregnated with the surgical material. In one embodiment, the surgical material forms a separate layer from the support material. In a further embodiment, the surgical material may be impregnated in the support material and also be present as a separate layer.

In one aspect, the device is sterile or sterilizable. The device may also be contained in a sterile package.

In one aspect, the device is in the form of a ribbon. The device in the form of a ribbon maybe of any suitable length to width ratio. In one aspect, the ribbon is of a length to width ratio of from about 10:1 to about 20:1. In one embodiment, the device in the form of a ribbon is from about 10-50 cm long and from about 0.5 to 5 cm wide. In various embodiments, the ribbon may be from about 10-40, 10-30, or 10-25 cm long and from about 1-2 or 1-3 or 2-5 cm wide. The thickness of the device in the form of a ribbon maybe from about 0.3 to 5 cm.

In one aspect, the surgical material is an extruded material. In one aspect, the extruded material is in the form of a ribbon that is from about 10-40, 10-30, or 10-25 cm long and from about 1-2 or 1-3 or 2-5 cm wide. The extruded material may be of any suitable thickness. In one aspect, the thickness of the extruded material is from about 0.1 to 0.5 cm, from about 0.1 to 1 cm, from about 0.1 to 2 cm, from about 0.1 to 3 cm, from about 0.1 to 4 cm, or from about 0.1 to 5 cm.

In accordance with any of the embodiments of the device described herein, the surgical material may be suitable for use as a mechanical hemostat, a bone void filler, a bone graft extender, a bone cement, or a tissue adhesive.

In one embodiment, the surgical material is in the physical form of a putty or a paste. In one embodiment, the surgical material is a material selected from the hemostatic materials described in any of U.S. Pat. No. 7,989,000 by Kronenthal (which describes compositions containing a solid particulate fatty acid salt suspended in a liquid poloxamer along with certain other excipients); U.S. Pat. No. 5,356,629 by Sander, (which describes a composition containing coated particles of polymethylmethacrylate in a matrix of cellulose ether, collagen, or hyaluronic acid); U.S. Pat. Nos. 7,553,913 and 7,829,616 by Wellisz, (which describes hydrophilic, water soluble, waxy compositions comprising a base of a random copolymer comprising ethylene oxide and one or more other alkylene oxide(s) which maybe mixed with solid particles); U.S. Pat. No. 7,914,819 by Wen, (which describes a polymeric matrix having a polysaccharide backbone); U.S. Pat. No. 7,074,425 by Constantine, (which describes hydrophilic polyethylene glycol based compositions consisting of a mixture of a high and a low molecular weight polyethylene glycol of HLB (hydrophilic/lipophilic balance) greater than 20); and WO 2013067154 by Knaack.

In one embodiment, the support material is a body absorbable or non-absorbable fabric material. The fabric material maybe woven or non-woven. In one aspect, the fabric material has an area density of from about 15 to 35 $g/m^2$. In one aspect, the fabric material has an area density of from about 18-25 $g/m^2$. In one aspect, the fabric material has an area density of about 16 $g/m^2$, 18 $g/m^2$, 20 $g/m^2$, 22 $g/m^2$, 24 $g/m^2$, 26 $g/m^2$, 28 $g/m^2$, or 30 $g/m^2$.

In one embodiment, the device consists of a 0.3 mm thick optionally pigmented fabric having an area density of about 22 $g/m^2$ knitted from 3-4 mil monofilament surgical polypropylene fiber. This fabric is cut into 24 cm by 2 cm pieces, between 2 pieces of which a ribbon of hemostatic putty, 22 cm long by 1 cm wide by 0.2 cm thick is centrally sandwiched.

In another embodiment, the device consists of a 0.3 mm thick optionally pigmented, absorbable fabric having a" area density of about 22 $g/m^2$ knitted from 3-4 mil monofilament polydioxanone fiber. This fabric is cut into 24 cm by 2 cm pieces, between 2 pieces of which a ribbon of hemostatic putty, 22 cm long by 1 cm wide by 0.2 cm thick is centrally sandwiched.

In another embodiment, the device consists of a 0.3 mm thick pigmented absorbable fabric having an area density of about 22 $g/m^2$ knitted from 3-4 mil monofilament Monocryl fiber. This fabric is cut into 24 cm by 2 cm pieces, between 2 pieces of which a ribbon of hemostatic putty, 22 cm long by 1 cm wide by 0.2 cm thick is centrally sandwiched.

In another embodiment, the device consists of a 0.3-0.5 mm thick optionally pigmented multifilament fabric having an area density of about 22 $g/m^2$ knitted from PGLA. This fabric is cut into various shapes and sizes, in which hemostatic putty is impregnated, e.g., 22 cm long by 1 cm wide by 0.3-0.5 mm thick.

In one embodiment, the device is sterile and contained within a package. For use, the device is removed from the package, preferably within a sterile surgical field. In one embodiment, where the device consists of a surgical material between two layers of support material, one layer of the support material is removed from one side of the surgical material and discarded. The surgical material, still supported on one side by the remaining layer of support material, is placed on the wound or at the surgical site and manually pressed into site.

The device as described herein may be used, for example, to achieve one or more of hemostasis, sealing, pain relief, delivery of therapeutic drugs, infection control, adhesion, bone growth/healing, fixation, a surgical adhesion barrier, to lend mechanical support, space filling and/or void filling, depending on the surgical material used. Accordingly, the surgical material of the device may comprise one or more of an osteoconductive agent, an osteoinductive agent, an analgesic, an antimicrobial agent, an adhesive agent, an anti-tumor therapeutic agent, a hemostatic agent, an anti-inflammatory agent, an anti-surgical adhesion agent, and/or a hardening material. The surgical material may also contain one or more other optional additives as described infra.

In one embodiment, the invention provides methods of sealing an anastomotic wound or surgical site by applying the device to the adjacent surfaces of the anastomosis. In one embodiment, the method comprises connecting and sealing a surgical anastomosis, the method comprising removing one layer of a support material to expose one surface of the surgical material, applying the exposed surface of the surgical material to at least one surface of the tissue anastomosis by pressing the exposed surface of the surgical material onto the surface of the tissue anastomosis until it adheres to the tissue, and then removing the second layer of support material from the surgical material, resulting in repair and sealing of the tissue. In one embodiment, the method comprises wrapping the device around a blood vessel or cut tissue and applying pressure until the device adheres to the blood vessel or cut tissue. In one embodiment, the invention provides a method for sealing a tissue, the method comprising applying the device in the form of an elongated ribbon to at least one cut edge of a tissue, e.g., a sternum, skull flap, or site of reapproximated tissues, applying pressure until the device adheres to the cut edge of the tissue, and bringing the other edge of the cut tissue into contact with the device, thereby sealing the tissue. The foregoing methods may also include steps of removing one layer of a support material to expose one surface of a surgical material, applying the exposed surface of the surgical material to at least one surface of the tissue by pressing the exposed surface of the surgical material onto the surface of the tissue until it adheres to the tissue, and then removing the second layer of support material from the surgical material, resulting in repair and sealing of the tissue.

In one embodiment, the invention provides methods of achieving mechanical hemostasis. In accordance with a method for mechanical hemostasis, the surgical material is pressed into the wound to achieve tamponade hemostasis. The term "tamponade" refers to the mechanical hemostasis occurring when a material is applied to a bleeding surface to occlude the vessels or pores through which blood flows, creating a static interface between the material and the dammed blood flow. Normal clotting can then occur within this static interface. Thus, in accordance with this embodiment, the surgical material must be suitable for use as a tamponade. In the case of hard tissues, such as bone, the material must adhere directly to the actively bleeding surface of cut bone, and not be easily dislodged by the force of flowing blood or by surgical irrigation, and must not be highly water-soluble such the cohesion of the material is lost in the aqueous environment of the wound site. Once hemostasis is achieved, support material is removed from the treated surface and discarded so that no support material remains in the wound. In another embodiment, where the surgical material is impregnated in the support material, the support material containing the surgical material is pressed directly into the wound, e.g., onto the bleeding wound surface, to achieve tamponade hemostasis and, if absorbable, the support material can optionally remain at the surgical site, or it can be removed and discarded. If the support material is non-absorbable, it is removed and discarded.

In one embodiment, the invention provides a method for mechanical hemostasis at a wound site, the method comprising wrapping the device around a blood vessel or cut tissue and applying pressure until the device adheres to the blood vessel or cut tissue. In one embodiment, the invention provides a method for mechanical hemostasis at a wound site, the method comprising applying the device in the form of an elongated ribbon to at least one cut edge of a tissue, e.g., a sternum, skull flap, or site of reapproximated tissues, and applying pressure until the device adheres to the cut edge of the tissue, thereby achieving mechanical hemostasis.

Device with Self-Assembling Peptide-Based Surgical Materials

The surgical material of the devices described herein may consist of one or more self-assembling peptides, or a composition comprising same, which assemble spontaneously into ordered nanostructures that are adhesive and/or mechanically hemostatic. Examples of suitable self-assembling peptides for use in the surgical materials are described in U.S. Pat. No. 8,022,178 (Horil et al.) and U.S. Pat. No. 8,299,032 (Yokoi et al.), which are incorporated herein by reference in their entireties. The '178 Patent describes RADA-16 which is a 16-amino acid peptide commercially available from Innovagen. The '032 Patent describes other peptides containing 12-32 amino acids, one peptide of which is commercially available from Menicon as PanaceaGel (13 amino acids). Both RADA-16 and PanaceaGel self-assemble in aqueous solution to form coherent, transparent beta-sheets which then form coherent nanofiber hydrogel networks containing up to 99+% water, Device with Isocyanate-Based Surgical Materials The surgical material of the devices described herein may consist of a curable composition, or multiple separate compositions, for example a pair of compositions, that are reactive with each other such that when the separate curable compositions are combined into a single composition, the single composition begins to cure. In one embodiment where the surgical material consists of a single curable composition, cure is initiated when the composition contacts the aqueous environment of the wound site. In either case, the surgical material (which may also be referred to as the curable surgical composition) cures into a fully hardened polymeric composition, the polymer selected from a polyurethane, a polyureaurethane, a polyetherurethane, or a polyesterurethane, over a period of time at body temperature (i.e., about 37 C). The period of time ranges from about 5 minutes to 96 hours.

In one embodiment, the surgical material is in a fully or partially cured state which is hard, relatively rigid and non-pliable, and is poorly adhesive or non-adhesive, and the surgical material is in contact with at least one surface of a support material. In the context of this embodiment, the surgical material, when heated to a temperature of between about 45 C to 75 C, softens and becomes more pliable and adhesive. The surgical material can then be shaped and applied to the wound site where, as it cools, it will return to a hardened, rigid form, non-adhesive (or low adhesive) form. In one embodiment, the support material is in the form of a mesh having at least one layer of the surgical material in contact with at least one surface of the mesh.

Each curable composition comprises an isocyanate component and a polyol/polyamine component (which may be referred to simply as "isocyanate" or "polyol/polyamine"). The isocyanate component consists of an isocyanate monomer, polymer, prepolymer, or combination thereof. The isocyanate component may thus comprise one or more different isocyanates, as well as an isocyanate in both its monomeric form and its polymer or prepolymer form. The polyol/polyamine component may also be in the form of a prepolymer, either entirely or partially (such that some unreacted polyol/polyamine remains in the composition) The term "isocyanate" is used generically to refer to isocyanates, diisocyanates, and polyisocyanates. The term "polyol" in the context of the "polyol/polyamine component" refers to both diols and polyols. Thus, the polyol or polyamine component may comprise or consist of one or more different diols, polyols, polyamines, or mixtures of two or more diols, polyols and/or polyamines. The isocyanates and polyol/polyamines that can be used in the surgical materials are described in more detail infra.

In one embodiment, the curable surgical material is able to set and adhere in aqueous environments. By nature, the isocyanate component, even containing hydrolysable linkages, is essentially hydrophobic and will resist dissolution in aqueous systems. This is true for certain diamines in this context. It has been found that making the diol more hydrophobic by adding a hydrophobic hydrocarbon-rich residue to a polyol, e.g., glyceryl-1 or 2-monostearate, a more water resistant system is obtained. A variation of this embodiment involves the substitution of a silicon-based moiety for the hydrocarbon-rich residue although this may affect absorbability. Alternatively hydrophobicity and setting rate in aqueous environments can be improved through the use of hydrophobic fillers such as insoluble or weakly soluble aliphatic molecules and salts thereof, including divalent salts, (eg calcium, magnesium, or zinc) of fatty acids. Also useful are cholesterol and its derivatives, as well as silated derivatives of ceramics or bone (Skimp et al., U.S. Pat. No. 7,270,813) Another embodiment of a water resistant, settable, surgical material adds a small amount of hydrophobic isocyanate to the relatively hydrophilic polyol component resulting in a water-resistant mixture of polyol containing a minor amount of hydrophobic polyurethane prepolymer. In one embodiment, the chain extender does not comprise an amino acid group.

The curable surgical compositions may further comprise an additive selected from one or more of tocopherol esters (e.g., tocopheryl acetate), triglycerides, acetyl triethyl citrate, and fatty acid esters, to aid in handling properties and packaging. In one embodiment, the curable surgical composition further comprises one or more additives selected from an antioxidant, an anhydrous particulate material, a colorant, a therapeutic agent, and a radiopaque agent. In one embodiment, the therapeutic agent is selected from one or more of an anticancer agent, an antimicrobial agent, an anesthetic agent, an analgesic agent, an anti-inflammatory agent, and an osteogenic agent.

In one embodiment, the curable surgical composition further comprises an osteoconductive component. In one embodiment, the osteoconductive component also confers porosity to the composition and the porosity is sufficient to allow the ingress of fluids and/or cells (e.g., osteoclasts, blood cells) into the composition in situ. In one embodiment, the osteoconductive component comprises or consists of particles of an osteoconductive material, such as particles of tricalcium phosphate or bioglass. The term bioglass refers to a group of glass-ceramic materials comprising $SiO_2$, $Na_2O$, $CaOP_2O_5$, and combinations of these.

In one embodiment, porosity is not introduced into the curable surgical composition as it cures by the addition of water or a carboxylic acid, e.g., benzoic acid, into any of the component parts of the composition. In one embodiment, the component parts do not contain either a carboxylic acid or added water such that the only water present during the curing reaction is water that may optionally be present at the site of implantation in the body.

In one embodiment, the fully hardened polyurethane or polyureaurethane composition possesses sufficient mechanical properties to be weight bearing, for example for use as a weight-bearing implant in bone, such as a bone void filler, or a bone cement.

In one embodiment, the curable surgical composition comprises a prepolymer. A prepolymer is a polymer having reactive end groups, e.g., isocyanate or hydroxyl groups. In one embodiment, the prepolymer comprises an excess of the isocyanate component relative to the polyol/polyamine component. In one embodiment of a two-component composition, one component comprises a prepolymer and no, Of substantially no, unreacted polyol; and the second comprises or consists of a hydroxyl terminated prepolymer lacking free isocyanate groups and unreacted polyol or polyamine.

A low molecular weight polymer refers to a polymer having a number average molecular weight in the range of about 500 to 20,000 or 500 to 10,000, A prepolymer containing reactive isocyanate end groups is formed, for example, from the initial reaction of an excess of isocyanate with a limiting amount of polyol or polyamine.

Each of the components may also independently comprise an optional particulate material and an optional chain extender, crosslinker, or curative.

As discussed above, the components of the settable composition are provided as individual units, each containing reagents in amounts such that when the components are mixed together, they form a mixture that fully reacts or cures into a hardened composition after a period of time at room or body temperature.

Each composition optionally contains an amount of particulate material suspended in the liquid components to form a composition having a putty-like consistency.

In one embodiment, the particulate material is selected from one or more of a polyurethane, calcium sulfate, calcium phosphosilicate, sodium phosphate, calcium aluminate, calcium phosphate, hydroxyapatite, demineralized bone, or mineralized bone. Other particulate materials may also be used, as described infra.

In one embodiment, the device comprises or consists of a surgical material and a support material, the surgical material being in the form of a ribbon or sheet and contained between two layers of the support material (e.g., a top layer and a bottom layer). In one embodiment, the support material is body-absorbable and in the form of a microporous or macroporous mesh, or in the form of a film, as described above. The surgical material is in the form of a putty, moldable by hand at room temperature. The putty material comprises one or more isocyanates, one or more polyols or polyamines, and a particulate material in an amount sufficient to impart the viscosity of a hand-moldable putty to the compositions, for example in an amount of from about 50 to 85 wt % based on the total weight of the composition. Suitable particulate materials are described above and it a further aspect, the putty material comprises unreacted monomeric isocyanate and a prepolymer consisting of the remaining isocyanate reacted with the polyol or polyamine component, such that the composition contains no free (unreacted) polyol or polyamine. In a specific embodiment, the putty material comprises from about 15-40% isocyanate, 0.5-4% polyol/polyamine, and 50-75% particulate material. In accordance with this embodiment is provided a method for wound closure, and/or for mechanical hemostasis, the method comprising removing one layer of support material from the device to expose a surface of the surgical material, applying the surgical material to the surface of the wound (e.g., cut bone) with sufficient pressure such that the surgical material adheres to the surface of the wound, and removing the second layer of support material prior to closing the wound. The surgical material will cure into a fully hardened polymeric material at the wound site in situ.

In another embodiment is provided a surgical device consisting of two component devices as described herein. In accordance with this embodiment, each component device, A and B, comprises or consists of a surgical material and a support material, the surgical material being in the form of a ribbon or sheet and contained between two layers of the support material (e.g., a top layer and a bottom layer). The support material is preferably body-absorbable and in the form of a microporous or macroporous mesh, or in the form of a film, as described above. The surgical material is in the form of a putty, moldable by hand at room temperature. The putty material comprises one or more isocyanates, one or more polyols or polyamines, and a particulate material in an amount sufficient to impart the viscosity of a hand-moldable putty to the compositions, for example in an amount of from about 50 to 85 wt % based on the total weight of the surgical material of each component device. The particulate material may be selected from the materials, and combinations thereof, as described above. The surgical material of each component device A and B is reactive such that when the surgical material of component device A contacts that of component device 13, a reaction is initiated which results in the curing of A and B into a single fully cured composition over a period of time.

In one aspect of this embodiment of a surgical device consisting of two component devices, the surgical material of component device A comprises 15-40% isocyanate, 0.5-5% polyol, and 50-75% particulate material, based upon total weight of the surgical material; and the surgical material of component device B comprises 1-10% of the isocyanate, 3-15% of the polyol, and 65-95% or 75-85% particulate material, based upon total weight of the surgical material. In one embodiment, the polyol in A is present in a prepolymer with the isocyanate component such that there is substantially no unreacted polyol in A and the isocyanate component in B is present in a prepolymer such that there is substantially no unreacted isocyanate in B.

In another aspect of this embodiment of a surgical device consisting of two component devices, the surgical material of component device A comprises 15-40% isocyanate, 0.5-5% of polyol, and 40-85% particulate material, based upon total weight of surgical material; and the surgical material of component device B comprises 1-1.0% isocyanate, 3-1.5% of polyol, and 65-95% or 75-85% particulate material, based upon total weight of the surgical material. In one embodiment, the polyol in A is present in a prepolymer with the isocyanate component such that there is substantially no unreacted polyol in A and the isocyanate component in B is present in a prepolymer such that there is substantially no unreacted isocyanate in B.

In another aspect of this embodiment of a surgical device consisting of two component devices, the surgical material of component device A comprises 15-50% isocyanate, 0.5-5% polyol, and 40-75% particulate material, based upon total weight of the surgical material; and the surgical material of component device B comprises 1-1.0% isocyanate, 3-15% polyol, and 65-85% particulate material, based upon total weight of the surgical material.

In another aspect of this embodiment of a surgical device consisting of two component devices, the surgical material of component device A comprises 20-35% isocyanate, 0.5-5% polyol, and 50-75% particulate material, based upon total weight of putty A; and the surgical material of component device B comprises 1-10% isocyanate, 3-15% polyol, and 75-85% particulate material, based upon total weight of the surgical material, The Isocyanate Component In one embodiment, the isocyanate component comprises or consists of an aromatic isocyanate, an aliphatic isocyanate, a cycloaliphatic isocyanate, or an adduct of an isocyanate, or a mixture of any of the foregoing, A mixture refers to a mixture of two or more of the foregoing. For example, the isocyanate component may comprise or consist of a mixture of two or more isocyanates independently selected from an aromatic isocyanate, an aliphatic isocyanate, a cycloaliphatic isocyanate, and an adduct of an isocyanate. In one embodiment, the isocyanate is an aliphatic isocyanate selected from the group consisting of ethyl lysine diisocyanate, hexamethylene diisocyanate, cyclohexyl diisocyanate.

In one embodiment, the isocyanate component of the curable surgical material comprises one or more isocyanates that are relatively non-absorbable. Such surgical materials are particularly suitable to soft tissue applications (absorbable materials being preferred for hard tissue applications). In one embodiment, the isocyanate is an aromatic isocyanate selected from diphenylmethanediisocyanate (MDI), including mixtures thereof such as mixtures of 2,4'-diphenylmethanediisocyanate and 4,4'-diphenylmethanediisocyanate isomers (ISONATE 50 OP, Dow Chemical Co. and RUBINATE 9433, Huntsman Corp.) and its pure 4,4-diphenylmethanediisocyanate form (MONDUR M, Bayer AG and RUBINATE 44, Huntsman Corp.), In one embodiment, the aromatic isocyanate is one of the commercially available polymeric isocyanates ISONATE 143L, ISONATE PAPI 901, and ISONATE PAPI 27 (Dow Chemical Co), These isocyanates, particularly the diphenylmethane derivatives, generally result in non-absorbable or slowly absorbable polyurethanes.

In one embodiment, the surgical material is fully or partially absorbable, and the isocyanate component comprises or consists of [5-[2-[2-(4-Isocyanatobenzoyl)oxypropanoyloxy]-ethoxy]-1-methyl-2-oxo-pentyl]-4-isocyanatobenzoate, or "ALD". In one embodiment, the two lactyl moieties of ALD each are racemic. Alternatively, these lactyl moieties may both have D or the L conformations. Alternatively, one lactyl moiety may be D while the other is L, or one may be D, L while the other is D or L. Such changes in stereochemistry may improve the physical and/or biological properties of the resulting polymer.

In one embodiment, the adduct of an isocyanate is selected from a hexamethylene diisocyanate trimer (DESMODUR N-3390) and a hexamethylene diisocyanate biuret (DESMODUR N-100) both commercially available from Bayer AG.

In one embodiment, the settable surgical material, which may be formed from a polymer selected from a polyurethane, a polyureaurethane, a polyetherurethane, or a polyesterurethane comprises at least one hydrolysable linkage. In one embodiment, the at least one hydrolysable linkage is derived from glycolic acid, lactic acid, caprolactone, or p-dioxanone. In one embodiment, the at least one hydrolysable linkage is selected from the group consisting of ester, amide, anhydride and sulfonamide linkages between the ester-urethane, urethane- or ureaurethane-containing groups. In one embodiment, the material comprises one or more glycolyl, lactyl, or caprolactyl hydrolysable ester linkages. In one embodiment, the material comprises one or more ethylene glycol, diethylene glycol, propane diol or butane diol hydrolysable ester linkages. In one embodiment, the material comprises one or more ethylene diamine, propane diamine, butane diamine, hexamethylene diamine and polyalkylene diamine hydrolysable amide linkages. In one embodiment, the material comprises one or more lactyl hydrolysable ester linkages and each asymmetric lactyl moiety present in the polymer is selected from one or more of the D, the L or the DL (racemic) stereoisomers, The Polyol/Polyamine Component The diols, polyols, and polyamines suitable for use in the polyol/polyamine component of the curable surgical materials are either degradable or non-degradable, or a mixture of the two. As used herein, the term "polyol" is meant to refer generically to diols and polyols, unless indicated otherwise. Generally, absorbable isocyanate based compositions are formed by the combination of an excess of the isocyanate component with the polyol/polyamine component. The relative amounts are calculated as the molar ratio of NCO groups of the isocyanate component (I) to the active hydrogen functional groups (H) (e.g., hydroxyl, amino, and mixtures thereof) of the polyol/polyamine component. Generally, the ratio of polyisocyanate to polyol/polyamine (I:H) is at least 0.5:1. In certain embodiments, the ratio is about 1:1, about 1.5:1, about 2:1, about 3:1, or about 4:1. In other embodiments, the ratio is about 5:1, about 8:1, about 10:1, about 20:1, or about 50:1.

In certain embodiments, the polyol/polyamine component is present in an isocyanate prepolymer in an amount of from about 0.5% to about 50% by weight of the prepolymer. In certain embodiments, the polyol/polyamine component is present in an amount of from about 0.5% to 10%, from about 10% to 20%, from about 20% to 35%, from about 25% to 40%, or from about 35% to 50% by weight of the prepolymer.

Polyols suitable for use include biocompatible, naturally occurring polyols, synthetic polyols, and mixtures thereof. In certain embodiments, the polyols comprise at least one ester group. In certain embodiments, the polyol comprises 2 to 4 ester groups or 5 to 10 ester groups. In one embodiment, the polyol has two or more hydroxyl groups. Suitable polyols include diols and polydiols having repeating units containing up to about 18 carbon atoms. Examples of suitable diols include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,8-octanediol and combinations thereof. Examples of preferred polydiols include polyethylene glycol with molecular weights of from about 500 to about 10000, polytetramethylene ether glycols, polyols derived from glycolide, lactide, trimethylenecarbonate, p-dioxanone and/or caprolactone with molecular weights of about 500 to about 10000.

In one embodiment, one or more alkylpyrrolidones (see e.g., U.S. Pat. No. 7,955,616) may be added to the polyol component to improve healing.

In one embodiment, the polyol is a synthetic polyol selected from a polycaprolactone polyol, polyester polyols, polyadipate polyols (e.g., poly(hexane-adipate) dial, poly (butane-adipate) diol, poly(ethylene/propylene-adipate) dial, poly(hexane/adipate/isophthalate diol)), and polyols that have been derived from a synthetic acid (e.g., isophthalic acid, maleic acid). An example of a suitable biocompatible synthetic polyol is a polycaprolactone diol that is commercially available from Dow Chemical under the trade name TONE 32 B8, or a polycaprolactone co-glycolide or a polycaprolactone co-lactide. Further non-limiting examples of suitable synthetic polyols include poly (oxypropylene) glycols, poly(oxotetramethylene) glycols, and poly(oxyethylene) glycols. In one embodiment, the synthetic polyol is selected from a polycaprolactone co-glycolide or a polycaprolactone co-lactide.

In one embodiment, the polyol is a naturally occurring polyol selected from castor oil and lesquerella oil, the polyols that may be obtained by chemical modification of naturally occurring vegetable oils (e.g., castor oil, olive oil, sesame oil, corn oil), naturally occurring oils that have been trans-esterified (e.g., a modified castor oil polyol that has been prepared by the transesterification reaction of natural castor oil with suitable crosslinkers (e.g., glycerol, trimethylolpropane, and the like) or with acids (such as adipic acid), and naturally occurring oils that have been hydrogenated. Further non-limiting examples of suitable naturally occurring polyols include the commercially available castor-oil-based polyols CASPOL5001, CASPOL1962, and CASPOL5004 (all available from CasChem., Inc.). In certain embodiments, the polyol is not a naturally occurring polyol such as castor oil and lesquerella oil.

In certain embodiments, an isocyanate prepolymer is combined with a polyamine to form a poly(urethane-urea). The polyamine may be a primary or secondary di-amine, or a hindered amine. Non-limiting examples of suitable polyamines include, hindered diamine (e.g., isophorone diamine, "IPDA"), 1,4-cyclohexyl diamine, 1,3-pentane diamine, and aliphatic secondary diamines, and mixtures thereof. In certain embodiments of the present invention, aliphatic diamines and cycloaliphatic diamines may be particularly suitable, and may offer improved biocompatibility. Commercially available examples of suitable polyamines include CLEARLINK 1000 (Dorf Ketal).

Amines including diamines that may be suitable for use in the preparation of polyurea and polyureaurethanes include but are not limited to polyethyleneimines, PEG amines with weight average molecular weights from about 500 to about 5,000, polyoxypropylenediamines available under the tradename JEFFAMINES (Huntsman Corporation, Houston, Tex.) and polyetherdiamines in general, spermine, spermidine, hexamethylenediamine, octamethylenediamine, decamethylenediamine, dodecamethylenediamine, hexadecamethylenediamine, octadecamethylenediamine, polyamidoamine dendrimers, dextrans, PEG-dextran conjugates, cysteines, proteins and peptides containing amines, non-biologically active symmetrical and asymmetrical diamino compounds containing saturated and unsaturated, substituted and unsubstituted alkyl, aryl and alkylaryl groups having from about 2 to about 18 carbon atoms. Further, the diamino compound can be synthesized containing a hydrolyzable link such as one or more ester groups to accelerate the rate of polymer degradation (absorption) in the body. The following structure exemplifies this concept for hexamethylenediamine: 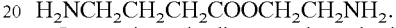

In certain embodiments, the polyol comprises 2 to 4 ester groups or 5 to 10 ester groups. Suitable polyols have at least two hydroxyl groups. In certain embodiments, the polyol has three or more hydroxyl groups making them crosslinkers.

The Chain-Extender/Crosslinker Component

In certain embodiments, one or more optional chain extenders or crosslinkers is incorporated in the curable surgical materials. In certain embodiments, only a chain extender is present. In other embodiments, both a chain extender and a crosslinker are present. In one embodiment, the one or more chain extenders is a low molecular weight polyhydroxyl- and/or polyamine-terminated compound having a molecular weight in the range of 10 to 500 Daltons and a functionality of at least two. In certain embodiments, the chain extender is a short-chain diol or diamine. In a particular embodiment, the chain extender or crosslinker is selected from glycerol, 1,4 butanediol, 1,6-hexanediol, diethylene glycol, and combinations thereof. Chain extenders having a functionality of three or more than three are also referred to as crosslinkers. In certain embodiments, the compositions of the invention are formed without crosslinkers and the compositions of the invention are not crosslinked. In other embodiments, the compositions of the invention are formed with one or more crosslinkers. The degree of crosslinking can be controlled, for example, by varying the amount of crosslinker present.

In certain embodiments, the chain-extender or crosslinker is present in an isocyanate prepolymer in an amount in the range of about 5% to about 80% by weight of the isocyanate prepolymer. In certain embodiments, the chain-extender or crosslinker is present in an amount of from about 5% to 20%, about 20% to 30%, about 30% to 40%, about 40% to 50%, about 50% to 60%, from about 60% to 70%, or from about 70% to 80% by weight of the isocyanate prepolymer.

The chain extender may be degradable or non-degradable. Preferably, at least one degradable chain extender is used. Suitable degradable chain extenders for use in the present invention are described in U.S. Patent Application Serial No. 2009/0082540, which is incorporated herein by reference. In one embodiment, the at least one degradable chain extender is HOCH$_2$CO$_2$CH$_2$CH$_2$OH or HOCH$_2$CO$_2$CH$_2$CH$_2$O$_2$CCH$_2$OH. 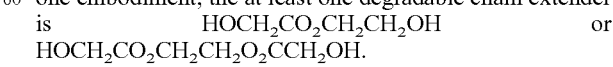

Other suitable chain-extenders or crosslinkers include natural or synthetic aliphatic polyols. Suitable polydiols for use in the present invention include diol or diol repeating units with up to 8 carbon atoms. Non-limiting examples include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof.

In other embodiments, the chain extender is a polyol selected from polyethylene glycol and polypropylene glycol having molecular weights of 500-10000 Daltons. Other examples include CASPOL1962 and CASPOL5004. In certain embodiments the preferred polydiols include polydiols selected from polyethylene glycol and polypropylene glycol with molecular weights of 500-10000. In some embodiments, the crosslinker is a non-absorbable crosslinker selected from triethanolamine (TEA), trimethylolpropane, and QUADROL (BASF Corp.). In some embodiments, the chain-extender is a non-degradable chain extender selected from 1,4-butanediol, 1,6-hexanediol, and diethylene glycol. The chain-extender or crosslinker may be present in an isocyanate prepolymer in an amount in the range of about 10% to about 80% by weight of the isocyanate prepolymer.

Water

In certain embodiments, the curable surgical material contains no added water. In some embodiments, the material is anhydrous. In certain embodiments where there is no added water, water may nevertheless be present in small amounts. For example, certain commercially-available polyols comprise a mixture of the polyol and a small amount of water. In addition, certain optional particulate materials as described herein, such as calcium carbonate, may comprise bound water. Formulating the compositions in an atmosphere that contains moisture may also result in the incorporation of water. In certain embodiments, the compositions are prepared under a nitrogen purge that comprises a desired amount of moisture, thereby controlling the water content of the compositions. In other embodiments, water may be added to the compositions during the process of their formation from the component parts. In other embodiments, the compositions are prepared under essentially water-free conditions with anhydrous components such that the resulting compositions are essentially anhydrous.

In certain embodiments, water is present in the compositions being made in an amount from at least about 0.01% to about 3% by weight of the composition. In certain embodiments, water is present in an amount of from about 0.05% to 1%, from about 0.05% to 1.5%, from about 0.1% to 1%, from about 0.1% to 1.5%, from about 0.1% to 2%, from about 1% to 2%, or from about 2% to 3%. In one embodiment, the amount of water is less than 3%, less than 2%, less than 1%, less than 0.5%, or less than 0.05%

Particulate Materials

The surgical material of a device as described herein, including the surgical materials comprising self-assembling peptides and the curable surgical materials described above, may contain optional particulate materials. In one embodiment, the particulate material is an osteoconductive material. In certain embodiments, the particulate material supports or promotes the growth of bone at the application site. In one embodiment, the particulate material is non-resorbable. In certain embodiments, the mean particle size of the optional particulate material is in the micron or submicron range. In one embodiment, the mean particle size is from about 0.001 to 0.100 microns, from about 0.100 to 5 microns, from about 5 to 100 microns, from about 5 to 500 microns, or from about 500 to 2000 microns.

In one embodiment, the optional particulate material is a carbonate or bicarbonate material. In one embodiment, the carbonate or bicarbonate material comprises or consists of one or more of calcium carbonate, magnesium carbonate, aluminum carbonate, iron carbonate, zinc carbonate, calcium bicarbonate, and sodium bicarbonate. In one embodiment, the optional particulate material comprises or consists of bone (e.g., demineralized bone, bone morphogenetic protein, allograft bone, and/or autogenous bone), calcium phosphate, siliconized calcium phosphate, substituted calcium phosphates (e.g., with magnesium, strontium, or silicate), calcium pyrophosphate, hydroxyapatite, polymethyl methacrylate, glass-ionomer, absorbable phosphate glass, calcium sulfate, tricalcium phosphate (e.g., beta tricalcium phosphate), or any combination of the foregoing. Other examples include one or more poly ether ether ketones (e.g., PEEK), REPLACE (Cortek, Inc.), EXPANCEL (Akzo Nobel). In other embodiments, the particulate material is a ceramic such as substituted calcium phosphates (e.g, silicate, strontium or magnesium substitution) or a glass such as bioglass. In one embodiment, the particulate material comprises or consists of one or more of calcium sulfate, calcium phosphosilicate, sodium phosphate, calcium aluminate, calcium phosphate, hydroxyapatite, demineralized bone, or mineralized bone.

The optional particulate material, when present, may comprise any one or more of the materials listed in the embodiments above. In one embodiment, the particulate material, if present in the composition, does not comprise calcium carbonate. In one embodiment, the particulate material may be polymeric such as a polyurethane.

In one embodiment, the particulate material is present in an amount of from about 0.01% to about 10% by weight of the composition. In certain embodiments, the optional particulate material is present in an amount of 0.10% to 10%, 1% to 10%, or 5% to 10%. In other embodiments, the optional particulate material is present in an amount of from about 10% to about 20% by weight of the composition, or from about 20% to 30%, about 30% to 40%, about 40% to 50%, about 50% to 60%, about 60% to 70% or about 70% to 80% by weight of the composition.

In one embodiment, the particulate additive material is graphene (available from Applied Graphene Materials and Thomas Swan, Ltd.), a single atomic layer of graphite that is electrically conductive, highly elastic, is about 100 times stronger than steel and which may be of value improving the quality of tissue healing and new bone stimulation.

Other Optional Additives

The surgical material of a device as described herein, including the surgical materials comprising self-assembling peptides and the curable surgical materials described above may also contain one or more optional additives.

The surgical materials may also optionally comprise one or more "cell openers." Non-limiting examples include ORTOGEL501 (Goldschmidt) and X-AIR (Specialty Polymers & Services). In certain embodiments, the cell openers are present in an amount in of from about 0.1% to 5% by weight of the composition. In one embodiment, the cell openers are present in an amount in of from about 1% to 2% or 1% to 3% by weight of the composition. Optional additives can be added to the magnesium based section but for the malonate/cyanoacrylate section, no active hydrogen atoms can be present including those in water because they will initiate polymerization.

The surgical material may also optionally comprise one or more therapeutic agents. In one embodiment, the one or more therapeutic agents are selected from an anti-cancer agent, an antimicrobial agent, an antibiotic, a local anesthetic or analgesic, a statin and an anti-inflammatory agent. In one embodiment, the antibiotic is selected from a broad spectrum antibiotic, such as gentamicin, clindamycin, and erythromycin, or a gram positive and gram negative family antibiotic such as an ampicillin and a cephalosporin. In one embodiment, the local anesthetic or analgesic is selected from lidocaine, bupivacaine, tetracaine, and ropivacaine. In one embodiment, the local anesthetic or analgesic is selected from lidocaine, benzocaine and fentanyl (a potent non-opioid anesthetic). In one embodiment, the one or more anti-inflammatory substances is selected from a non-specific anti-inflammatory such as ibuprofen and aspirin, or a COX-2 specific inhibitor such as rofecoxib and celeboxib.

In one embodiment, the surgical materials may further comprise one or more of an antioxidant, a colorant, a steroid, calcium stearate, tocopheryl acetate, and triacetin. In one embodiment, the antioxidant is selected from IRGANOX 1010 and IRGANOX 1035 (Ciba Geigy), and CYANOX 1790 and CYANOX 2777 (Cytec Industries). In certain embodiments, the antioxidant is present in an amount of from about 0.01% to 0.5% by weight of the composition. In one embodiment, the steroid is a steroid-based compound, such as an intracellular messenger, effective to modulate the rate of tissue growth, including bone growth. In one embodiment, the compositions further comprise one or more growth factors, for example BMP-2, BMP-7, PDGF, EGF, etc.

In one embodiment, the surgical material comprises one or more of calcium stearate, tocopheryl acetate, and triacetin, each present in a component putty of the composition in an amount ranging from 0.1 to 7% based upon the weight of the component putty. Non-limiting examples of colorants that may be included in the compositions are gentian violet, D&C Violet #2, and D&C Green #6.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1 (Soft Tissue)

To provide reinforcement to weakened soft tissue, a monofilament polypropylene mesh with a pore size of 1 mm was spray coated with a solution of 40% ALD, 20% Polyethylene glycol (300) and 40% methylene chloride. Following evaporation of the methylene chloride solvent, the gel was sufficiently coherent to hold the mesh in place until it was incorporated into normal body proteins. Its absorption rate was not determined.

Example 2 (Soft Tissue)

To provide hemostasis to soft tissue, a monofilament polylactide mesh with a pore size of 10 micron was spray coated with a solution of 40% ALD 20% Polyethylene glycol (300), 10% chitosan (microparticulate) and 30% methylene chloride. Following evaporation of the methylene chloride solvent, the implant was hemostatic to lacerated soft tissue upon application. Its absorption rate was not determined.

Example 3 (Soft Tissue, Self-Assembling Peptides)

To provide reinforcement to weakened soft tissue, a 3.5 square inch knitted monofilament polypropylene mesh was placed on the surface of the tissue to be reinforced, in this case muscle, and coated with 5.75 ml. of a 0.5% aqueous solution of PanaceaGel which formed a transparent gel within 2 minutes following application. The gel was sufficiently coherent to hold the mesh in place until it was incorporated into normal body proteins. Its absorption rate was not determined.

Example 4 (Hard Tissue, Self-Assembling Peptides)

To provide hemostasis to a bleeding bone surface, 2.5 ml. of a RADA-16 aqueous solution (0.8%) was applied to a bleeding bone surface and coagulated into a transparent gel which stopped the blood flow in 17 seconds. The gel was absorbed within 72 hours.

Example 5 (Hard Tissue, Isocyanate-Based Surgical Material)

In order to reapproximate adjacent segments of bone tissue, a device consisting of a ribbon of putty composed of 37% ALD, 2.5% PCL900, 6.5% Triacetin and 54% hydroxyapatite sandwiched between two layers of polyvinylchloride (PVC) non-porous film was used. One layer of PVC film was removed from the device to expose a surface of the putty. The putty edge was pressed into one of the two sternal edges following a medial sternotomy. The second PVC layer was then peeled away, leaving the putty adhered to the edge of the sternum. This action was repeated for the second sternal edge. The sternum was then wired closed, excess putty was removed and the entire sternum was incubated at 37 C in phosphate buffered saline. Following 24 hours, the wiring was removed and the putty material was found to have cured into a fully hardened material at the wound site in situ that was sufficiently coherent to hold the sternal edges together. Its absorption rate was not determined.

Example 6 (Hard Tissue, Isocyanate-Based Surgical Material)

In order to reapproximate adjacent segments of bone tissue, a device consisting of a ribbon of putty composed of 37% ALD, 3% PCL300, and 60% hydroxapatite sandwiched between two layers of polyethylene (PE) non-porous film was used. One layer of PE film was removed from the device to expose a surface of the putty. The putty edge was pressed into the edges of a cranial skull flap. The second PE layer was then peeled away, leaving the putty adhered to the edge of the skull flap. The skull flap was manually reapproximated into the surrounding cranium, excess putty was removed and the cranium was incubated at 37 C in phosphate buffered saline. Following 24 hours, the putty material was found to have cured into a fully hardened material at the wound site in situ that was sufficiently coherent to hold the skull flap in place. Its absorption rate was not determined.

Example 7 (Hard Tissue, Isocyanate-Based Surgical Material)

In order to reapproximate adjacent segments of bone tissue, a device consisting of A) a ribbon of putty composed of 37% ALD, 2.5% PCL900, 6.5% Triacetin and 54% hydroxapatite sandwiched between two layers of polyvinylchloride (PVC) non-porous film and B) a second ribbon of putty composed of 5% ALD, 8% PCL900, 4.5 Tocopherol Acetate 3.5% Triacetin and 79% calcium stearate sandwiched between two layers of polyvinylchloride (PVC) non-porous film, was used. One layer of PVC film was removed from the device to expose a surface of the putty A. The putty edge was pressed into one of the two sternal edges following a medial sternotomy. The second PVC layer was then peeled away, leaving the putty adhered to the edge of the sternum. This action was repeated for the second sternal edge using the films sandwiching the ribbon of putty B. The sternum was then wired closed, excess putty was removed and the entire sternum was incubated at 37 C in phosphate buffered saline. Following 24 hours, the wiring was removed and the putty material was found to have cured into a fully hardened material at the wound site in situ that was sufficiently coherent to hold the sternal edges together. Its absorption rate was not determined.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A surgical device in the form of a fabric or film that provides mechanical assistance for the application of a surgical material to a wound or surgical site, the device comprising a ribbon or sheet of surgical material selected from the group consisting of a hemostatic material, a hone void filler, a bone graft extender, a bone cement, a surgical sealant, a surgical adhesion barrier, an anti-surgical adhesion agent, an antimicrobial, an analgesic, an antineoplastic, an anti-inflammatory, a radiopaque, an osteoconductive material, an osteoinductive material, and any combination thereof, and a support material selected from the group consisting of a fabric or a film material, wherein the support material comprises two separate layers that surround the surgical material, wherein the surgical material is a composition in the form of a putty that is moldable and shapeable at room temperature and suitable for the mechanical hemostasis of hard tissue.

2. The surgical device of claim 1, wherein the surgical material is a high viscosity or a low viscosity material.

3. The surgical device of claim 1, wherein the surgical material is a composition in the form of a paste.

4. The surgical device of claim 1, wherein the support material is constructed from a non-absorbable fabric or a non-absorbable polymeric film material of low surface energy.

5. The surgical device of claim 4, wherein the fabric or film material is dyed or pigmented.

6. The surgical device of claim 5, wherein the fabric is non-absorbable and is knitted or woven.

7. The surgical device of claim 4, wherein the polymeric film material is constructed from one or more of a polyurethane, a poly(propylene), a poly(tetrafluorethylene), or a polysiloxane.

8. The surgical device of claim 1, wherein the surgical material is non-body absorbable, body absorbable, or partially body absorbable.

9. A method for mechanical hemostasis of actively bleeding soft or hard tissue, the method comprising applying an exposed surface of surgical material present in the surgical device of claim 1 to at least one surface of the bleeding tissue by pressing the exposed surface of the surgical material onto the surface of the tissue until is adheres to the tissue, thereby resulting in mechanical hemostasis of the bleeding soft or hard tissue.

10. The method of claim 9, wherein, when the bleeding tissue is a soft tissue, the surgical material is a low viscosity material.

11. The method of claim 9, wherein prior to use, a first layer of the support material is removed from the surgical material to produce the exposed surface.

12. The method of claim 11, wherein following application, the second layer of the support material is removed from the surgical device following adhesion of the surgical material.

13. A method for connecting and sealing a surgical anastomosis, the method comprising applying an exposed surface of the surgical sealant present in the surgical device of claim 1 to at least one surface of the tissue anastomosis by pressing the exposed surface of the surgical material onto the surface of the tissue anastomosis until it adheres to the tissue, thereby resulting in connection and sealing of the tissue.

14. The method of claim 13, wherein prior to use, a first layer of the support material is removed from the surgical material to produce the exposed surface.

15. The method of claim 14, wherein following application, the second layer of the support material is removed from the surgical device following adhesion of the surgical material.

16. A method for prevention of surgical adhesions of soft tissue, the method comprising applying an exposed surface of surgical material present in the surgical device of claim 1, wherein the surgical material comprises a surgical adhesion barrier or an anti-surgical adhesion agent, to at least one surface of the soft tissue by pressing the exposed surface of the surgical adhesion barrier or the anti-surgical adhesion agent onto the surface of the soft tissue until is adheres to the soft tissue, thereby preventing the formation of surgical adhesions on soft tissue.

17. The method of claim 16, wherein, when the bleeding tissue is a soft tissue, the surgical material is a low viscosity material.

18. The method of claim 17, wherein prior to use, a first layer of the support material is removed from the surgical material to produce the exposed surface.

* * * * *

UNITED STATES PATENT AND TRADEMARK OFFICE
CERTIFICATE OF CORRECTION

PATENT NO. : 10,751,036 B1
APPLICATION NO. : 16/165339
DATED : August 25, 2020
INVENTOR(S) : John Pacifico et al.

Page 1 of 1

It is certified that error appears in the above-identified patent and that said Letters Patent is hereby corrected as shown below:

In the Claims

At Column 19, Claim number 1, Line number 44:
"from the group consisting of a hemostatic material, a hone"
Should read:
-- from the group consisting of a hemostatic material, a bone --

Signed and Sealed this
Fifteenth Day of December, 2020

Andrei Iancu
*Director of the United States Patent and Trademark Office*